(12) United States Patent
Dobler

(10) Patent No.: US 11,103,610 B2
(45) Date of Patent: Aug. 31, 2021

(54) FRAGRANCE CARD WITH WINDOWED CONTAINER

(71) Applicant: Sven Dobler, Huntington, NY (US)

(72) Inventor: Sven Dobler, Huntington, NY (US)

(73) Assignee: Orlandi, Inc., Farmingdale, NY (US)

( * ) Notice: Subject to any disclaimer, the term of this patent is extended or adjusted under 35 U.S.C. 154(b) by 0 days.

(21) Appl. No.: 14/756,483

(22) Filed: Sep. 9, 2015

(65) Prior Publication Data

US 2016/0000957 A1 Jan. 7, 2016

Related U.S. Application Data

(60) Continuation-in-part of application No. 13/986,594, filed on May 16, 2013, now abandoned, which is a division of application No. 12/657,743, filed on Jan. 26, 2010, now abandoned.

(60) Provisional application No. 61/690,212, filed on Jun. 21, 2012.

(51) Int. Cl.
| | | |
|---|---|---|
| *A61L 9/12* | (2006.01) | |
| *A61L 9/04* | (2006.01) | |
| *A61L 9/00* | (2006.01) | |
| *A61L 2/00* | (2006.01) | |

(52) U.S. Cl.
CPC ........ *A61L 9/12* (2013.01); *A61L 2/00* (2013.01); *A61L 9/00* (2013.01); *A61L 9/04* (2013.01); *A61L 2209/134* (2013.01); *A61L 2209/15* (2013.01)

(58) Field of Classification Search
CPC .......... A61L 9/00; A61L 9/12; A61L 2209/00; A61L 9/04; A61L 2/00
USPC ...... 239/34, 60, 6, 8, 13, 53, 55, 42, 43, 57, 239/36, 51.5, 47, 56, 59
See application file for complete search history.

(56) References Cited

U.S. PATENT DOCUMENTS

| | | | |
|---|---|---|---|
| 2,757,957 A * | 8/1956 | Samann | A01M 1/2055 239/53 |
| 3,065,915 A | 11/1962 | Samann | |
| 4,419,395 A | 12/1983 | Sugimoto | |
| 4,883,692 A | 11/1989 | Spector | |
| 5,529,243 A | 6/1996 | Hoyt et al. | |
| 5,569,511 A | 10/1996 | Spector | |
| 5,853,672 A | 12/1998 | Lorman et al. | |
| 6,367,184 B1 | 4/2002 | Kheder | |
| 7,926,735 B1 * | 4/2011 | Mobley | A61L 9/04 239/53 |
| 2008/0023569 A1 * | 1/2008 | O'Leary | A61L 9/04 239/44 |
| 2008/0099576 A1 | 5/2008 | Hart | |

OTHER PUBLICATIONS

Ludacer, Randy, Black Ice Car-Freshener, 2008, Beach Packaging Design, https://beachpackagingdesign.com/boxvox/black-ice-car-f (Last visited Oct. 5, 2020). (Year: 2008).*

* cited by examiner

*Primary Examiner* — Alex M Valvis
*Assistant Examiner* — Christopher R Dandridge
(74) *Attorney, Agent, or Firm* — Paul M. Denk

(57) ABSTRACT

This invention is a fragrance card, with an attachment device, located within a container, that incorporates a window, which when removed, allows the fragrance of the impregnated card to be released into the ambient atmosphere.

1 Claim, 5 Drawing Sheets

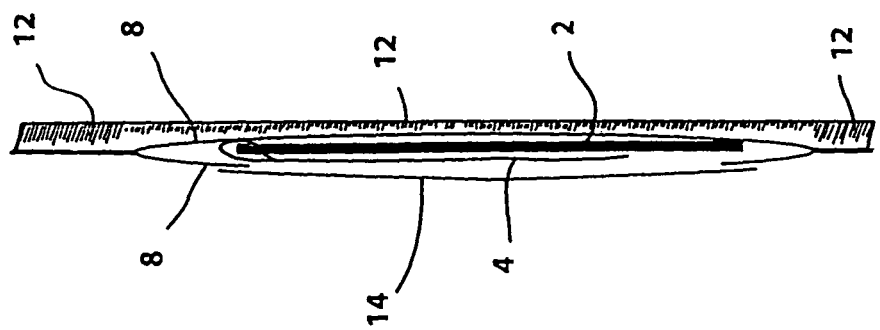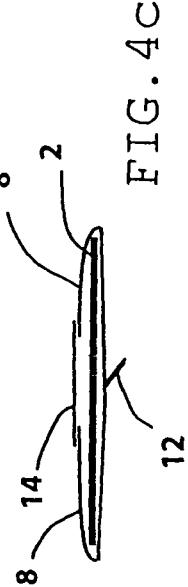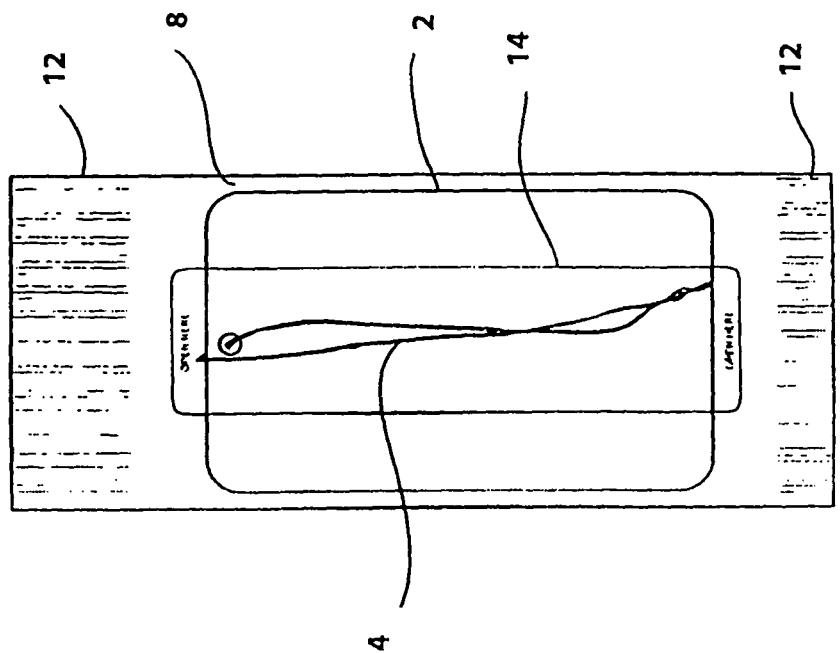
FIG. 4b
FIG. 4c
FIG. 4a

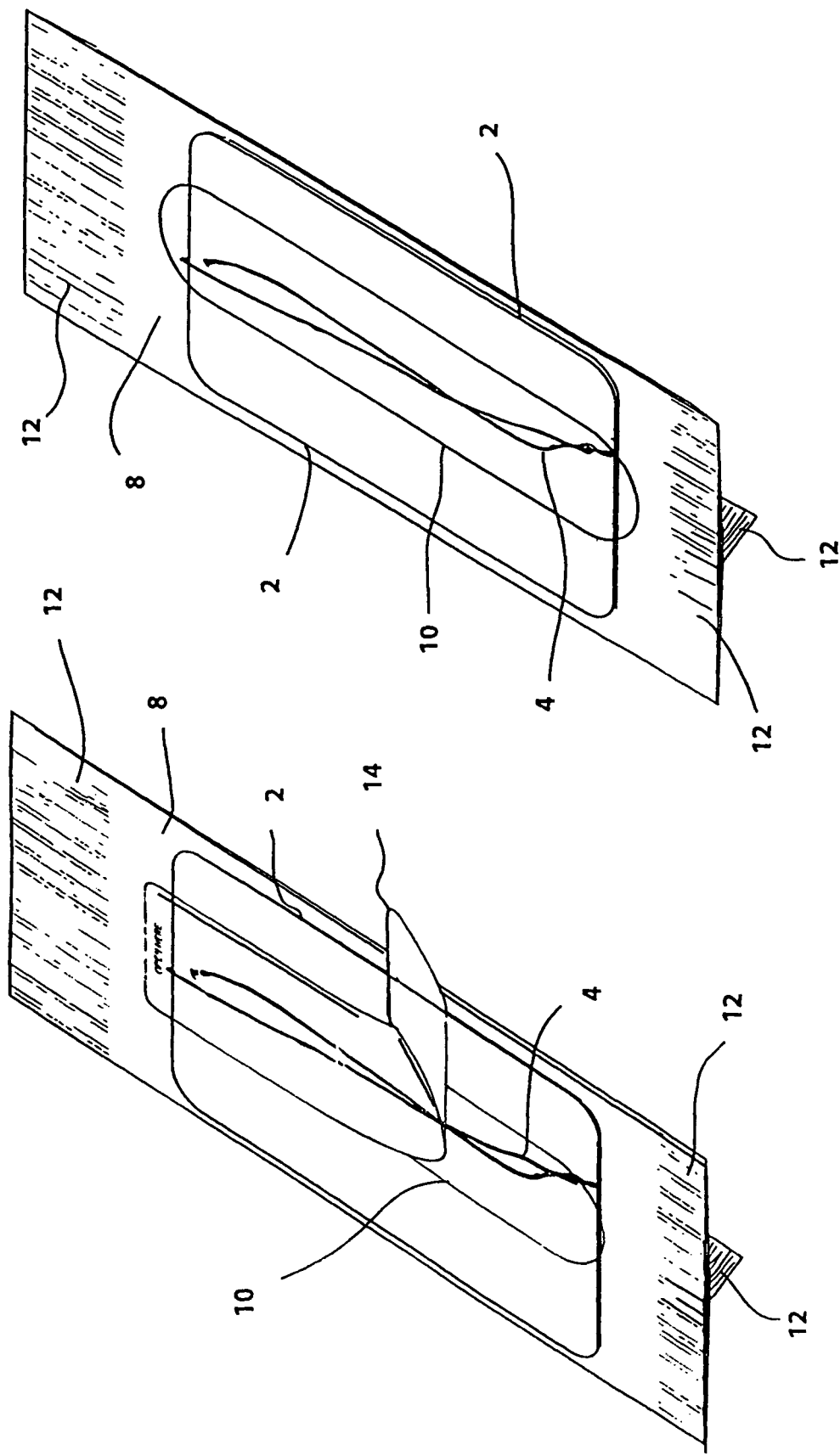

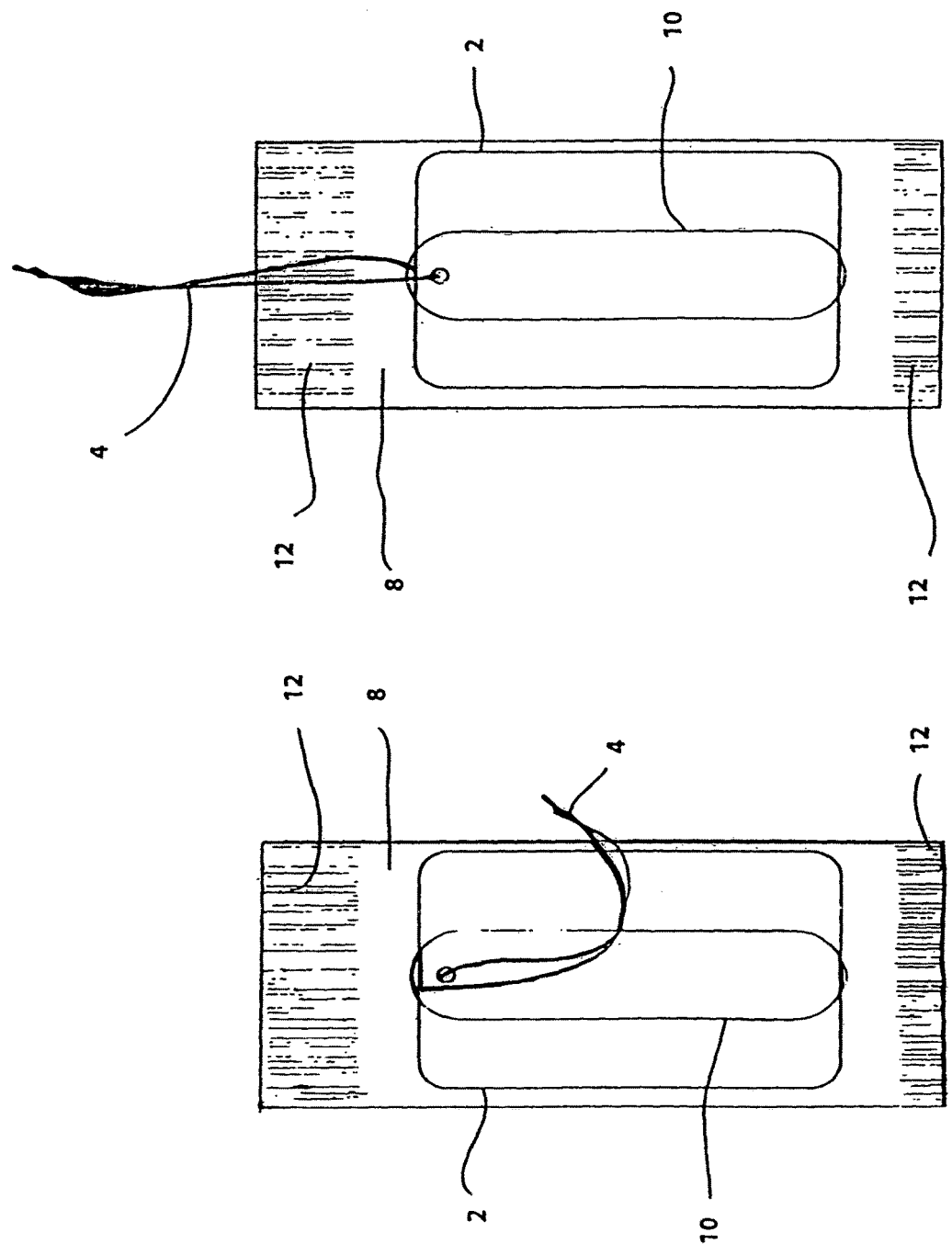

FRAGRANCE CARD WITH WINDOWED CONTAINER

CROSS REFERENCE TO RELATED APPLICATION

This continuation-in-part patent application claims priority to the non-provisional patent application having Ser. No. 13/986,594, filed on May 16, 2013, which claims priority to the provisional patent application having Ser. No. 61/690,212, filed on Jun. 21, 2012, which claims priority to the non-provisional patent application having Ser. No. 12/657,743, filed on Jan. 26, 2010, now abandoned.

FIELD OF THE INVENTION

This invention relates to a fragrance card, and one which incorporates a suspension system, incorporating a cord, which is contained by the sealing window that maintains the fragrance card sealed within its container, as to such time as the windowed container is removed, exposing the cord for suspension, and releasing the fragrance to the ambient atmosphere.

BACKGROUND OF THE INVENTION

Air fresheners have become widely popular in the last twenty years. They are produced in a wide range of fragrances and as well as shapes and sizes. They are used in a variety of locations form large rooms to small rooms to automobiles. Personal preferences in both the type of fragrance and the strength of the fragrance very widely. In addition to making a wide range of fragrances available it would be desirable to be able to control the rate or the amount of fragrance that was released in a given time. This would not only satisfy the personal preference of the user, but would conserve the fragrance making a fixed amount last for a longer period of time.

A particular type of fragrant air freshener that has become popular is one that is made of absorbent material and saturated with a volatile fragrant substance. This type of air freshener is referred to herein as a fragrance card. These fragrance cards are inexpensive, compact and disposal. The fragrance card is typically provided with a cord by which to hang the device in a room or automobile. The cord allows the fragrance card to be suspended, not only to improve volatilization of the fragrance, but also to allow the user to limit their physical contact with the fragrance card. The volatile materials and solvents that are impregnated in the air fragrance card are often oily, sticky, or possess such an intense aroma that the user may find it difficult to remove from their hands. The cord provides a means to handle the fragrance card with minimal direct contact. For these same reasons, it is also desirable that the fragrance card be contained in packaging that is easy to open and that the cord is easily and directly assessable after opening.

A number of efforts have been made to address the issues of controlled release of fragrance or packaging that limits the user's direct contact with the fragrance card. For example U.S. Pat. No. 2,757,957, separates the cord from the fragrance card within the container. However, the user is likely to tear the container and the container is not designed to regulate the fragrance after opening. U.S. Pat. No. 3,065,915 provides a container which may regulate the fragrance after opening but its use is limited to a fragrance card with a particular shaped. It requires a ridged and pointed fragrance card in order to pierce the container. It also does not allow easy access to the cord after opening. There is also a more recent patent that has issued upon a Fragrance Package, Dispenser, and Method, in the United States Patent Office, U.S. Pat. No. 7,926,735. But, there is no suggestion that it may be used as a display or hung or used in an automobile. What is needed is an inexpensive and easy to fragrance card and packaging that limits direct contact by the user, controls release of the fragrance after opening, and may also be used in combination with the hanging fragrance cards of different shapes.

SUMMARY OF THE INVENTION

This invention contemplates the formation of a fragrance card, which is attached to a suspension means, such as a cord or string, which is embodied within a wrapper like container, that incorporates a window and heat sealed seams. The fragrance card is within the wrapper like container, and the window has a cover thereover, with a cord beneath it, and the window cover can be peeled for removal, to expose the cord for suspension of the card, and to allow the fragrance impregnated upon the card to be released into the ambient atmosphere.

It is, therefore, the principle object of this invention to provide a fragrance card that can be maintained and sealed closure, but when opened, allows its fragrance to be released, while simultaneously providing a means for its suspension during usage.

These and other objects may become more apparent to those skilled in the art upon review of the invention as provided herein, and upon undertaking a study of the description of the preferred embodiment.

BRIEF DESCRIPTION OF THE DRAWINGS

In referring to the drawings:

FIG. 4*a* illustrates a front view of the apparatus in FIG. 3;

FIG. 4*b* illustrates a side view of the apparatus in FIG. 3;

FIG. 4*c* illustrates an end view of the apparatus in FIG. 3;

FIG. 5 illustrates a prospectus view of apparatus with the window cover being removed;

FIG. 6 illustrates a prospectus view of the fragrance card in the container with the window cover removed;

FIG. 7 illustrates the cord being removed through the window of the container;

FIG. 8 illustrates the fragrance card and container being suspended for use;

DESCRIPTION OF THE PREFERRED EMBODIMENT

Figure 1:
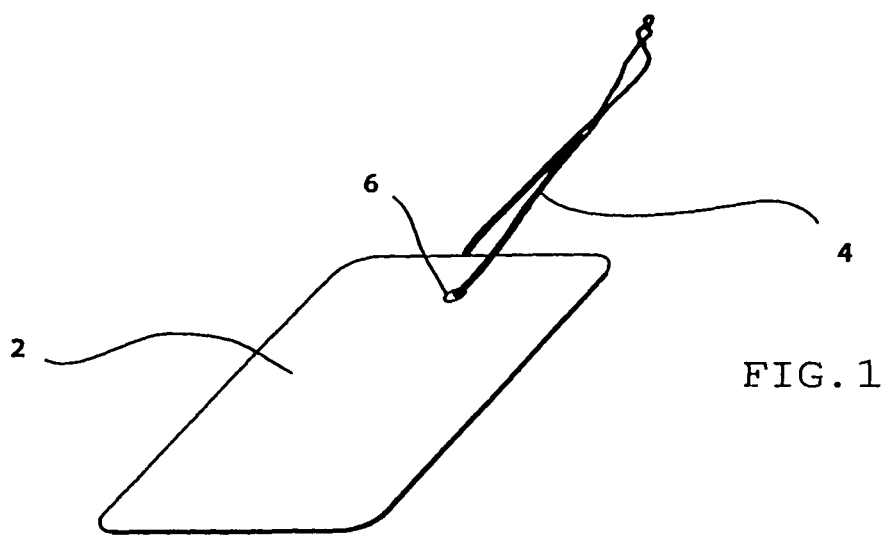
FIG. 1 illustrates a prospectus view of a fragrance card attached to a cord or string.

As illustrated in the figures, a preferred embodiment of the instant invention is a fragrance card 2 with an attached cord 4 packaged within a container 8, the container being non-porous and comprising a window 10 to allow vaporization of the fragrance. The window 10 of the container 8 is sealed with a window cover 14 until use to retain the fragrance of the fragrance card 2. Upon removal of the window cover 14, the user gains access to the cord 4, attached to the fragrance card 2. The cord 4 enables the user to suspend the fragrance card 2 while avoiding direct contact between the user and the fragrance card 2. The fragrance card 2, being larger than the window 10, retains the container 8 which then functions as a fragrance limiting device. The window cover 14 once removed from the window 10, partially exposes the fragrance card 2 to the ambient air, and allows dispersal of the fragrance at a rate predetermined by the size of the window 10 and the aromatic nature of the fragrance. The preferred embodiment will work with a fragrance card of any shape.

Figure 2:
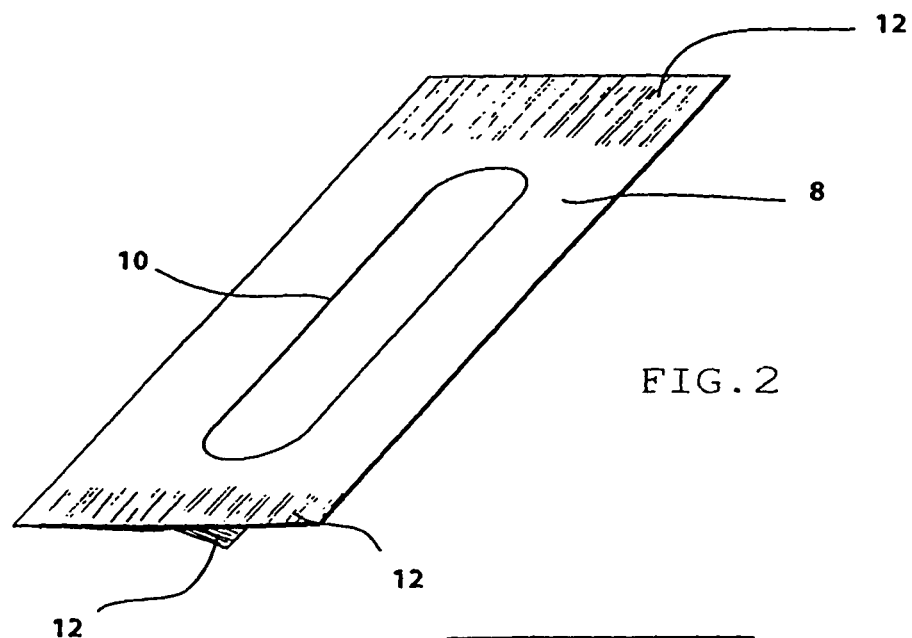
FIG. 2 illustrates a prospectus view of a wrapper like container with a window and heat sealed seams.
Figure 3:
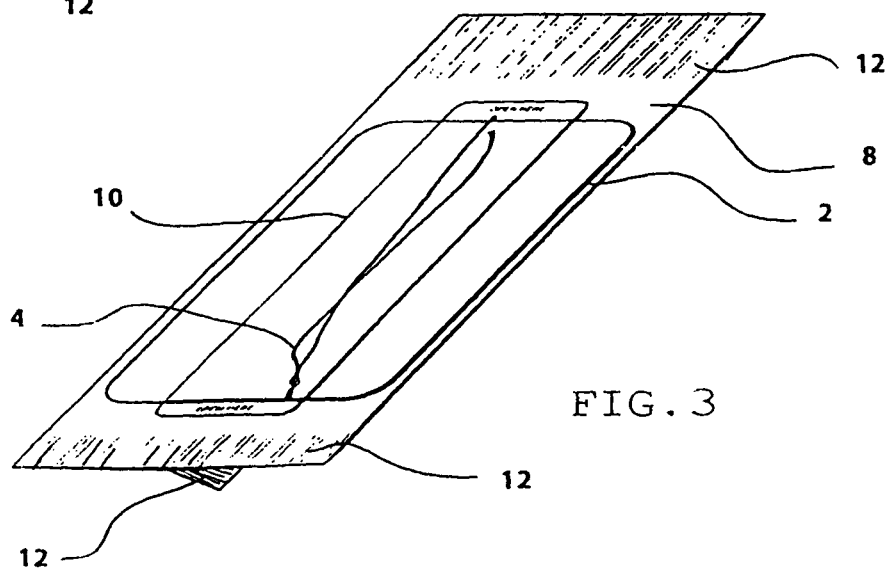
FIG. 3 illustrates a prospectus view of a fragrance card within a wrapper like container with a window cover over the window and a cord positioned behind the window cover.

Turning to the figures more specifically, illustrated in FIG. 1 is a fragrance card 2 attached to a cord 4. The means of attachment 6 illustrated in FIG. 1, is a hole through the fragrance card 2 by which the cord 4 may be tied, but it is anticipated the attachment may be of any means known in the art including fasteners, staples, adhesives, and alike. Illustrated in FIG. 2 is a non-porous wrapper like container 8, comprising at least one window 10 on a substantially flat surface of the container 8. The container 8, being manufactured from a simple sheet of non-pours material, typically comprises seams that must be sealed. Illustrated in FIG. 2, at each end and on one surface of the container 8, are seams that are preferably heat sealed 12. Illustrated in FIG. 3 and FIG. 4a-c is the fragrance card 2 and attached cord 4 enclosed within the container 8. The container 8 is preferably transparent, but may be semi-transparent or opaque. The container 8 contains one or more windows 10 which allow vaporization of the fragrance when in use. As illustrated in FIG. 3 and FIG. 4a-c, a non-porous window cover 14, being slightly larger than the window 10, is adhesively and reversibly attached to the container 8 so as to cover the window 10 and provide a non-porous seal that is continuous with the container 8. The container 8, with the window cover 14 in place over the window 10, provides a hermetically sealed container to prevent release of the fragrance from within the container to the surrounding atmosphere, until removal of the window cover 14. As illustrated in FIG. 3 and FIG. 4a-c, the cord 4 is attached to the fragrance card 2 and positioned within the container 8 so as to be co-located with the window 10, such that removal of the window cover 14 will allow the user direct easy access the cord 4. Illustrated in FIG. 5 is the window cover 14 being removed from the container 8 in a pealing motion. Although FIG. 5 shows the window cover 14 being removed from the bottom it is appreciated that the window cover 14 may be removed from the top, side or any direction. FIG. 6 shows direct access to the cord 4 after removal of the window cover 14. FIG. 7 illustrates the cord 4 being extracted from the container 8 through the window 10. FIG. 8 illustrates the cord 4 and fragrance card 2 in the suspended position with the container 8 being retained by the fragrance card 2 to limit the vaporization of the fragrance according to the size of the window 10, which is predetermined by the manufacturer to allow vaporization of the fragrance at an optimum rate.

Figure 10:
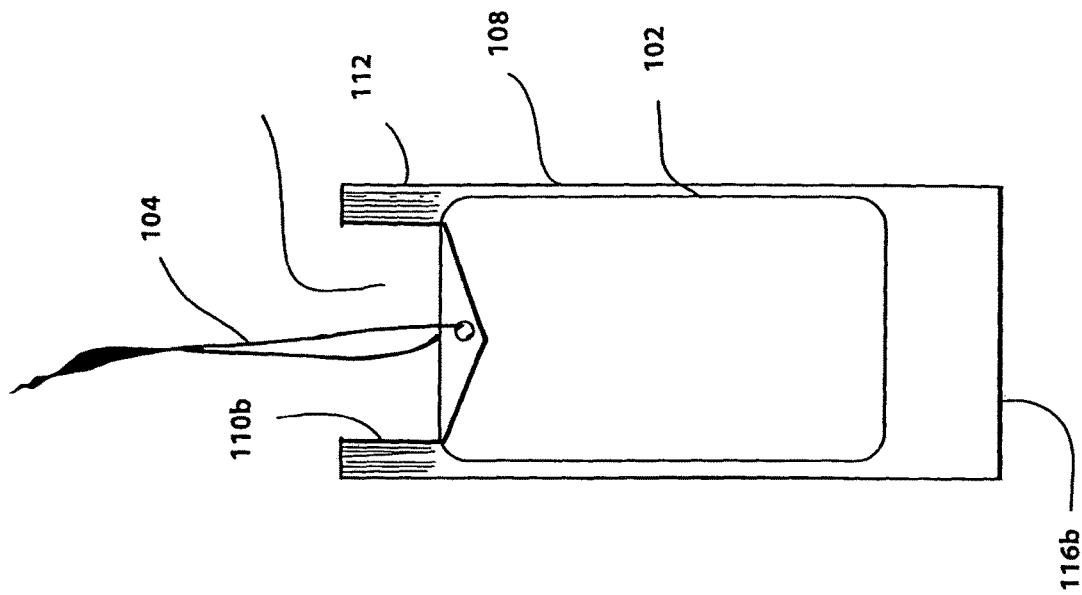
FIG. 10 illustrates the apparatus of FIG. 9, after the user has cut a window at the location identified by the window designator in FIG. 9, and after the user has cut an additional window at the location identified by the additional window designator in FIG. 9, and after the user has suspended the apparatus for use.
Figure 9:
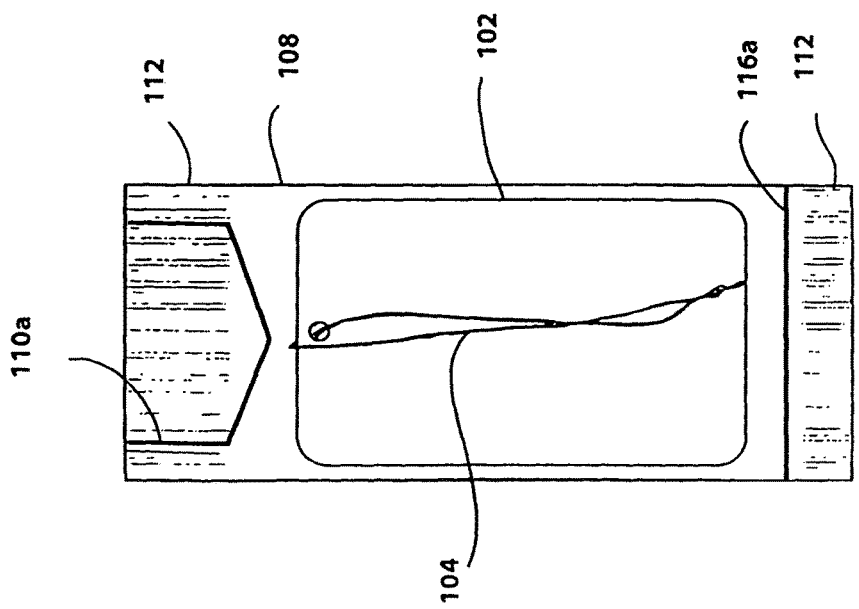
FIG. 9 illustrates an air fragrance card and container with a window designator identifying the size and location of the window for the user.

In another embodiment, the container may contain more than one window. Each window may be covered by a separate window cover, or one window cover may cover multiple windows. The cord will necessarily be co-located with one of the windows. This embodiment would allow the user to remove the one or more window covers as desired to control the amount of fragrance released. Illustrated in FIG. 9 and FIG. 10 is yet another embodiment of a method of controlling the rate of fragrance release utilizing a hanging fragrance card maintained in a non-porous container. FIG. 9 illustrates a fragrance card 102 within a container 108. The container is non-porous 108, but does not comprise a pre-manufactured window or window covers. The container 108 comprises a window designator 110a which is indicated to the user. The user will be instructed to create a window 110b by cutting the non-pours container 108 at a position designated by the window designator 110a. The window designator 110a instructs the user to cut a window that is necessarily smaller than the fragrance card 102 and is at a location near the cord 104. After cutting the window 110b the user gains access to the cord 104 which the user may use to suspend the fragrance card 102 and container 108 as illustrated in FIG. 10. The fragrance card 102, being larger than the window 110, retains the container 108 which then functions as a fragrance limiting device. Vaporization of the fragrance will be limited by the container 108 according to the size of the window 110b which has been predetermined by the manufacturer. As shown in FIG. 10, the user may also be instructed to cut an additional window 116b in the container 108, as desired to increase vaporization of the fragrance. The user may be instructed to cut one or more additional window 116b, which may be indicated by an additional window designator 116a. In FIG. 9, the additional window designator 116a designates cutting the container 108 between the bottom of the fragrance card 102 and the heat seal 112 to further expose the fragrance card 102 to the ambient air. At a later time similar additional windows may be cut by the user to further expose the fragrance card as the fragrance becomes depleted. It is anticipated that instructions educating the user how to practice the instant invention, including the size and position of the windows, will accompany the fragrance card 102 and container 108. The window designator 110a and/or additional window designator 116a may or may not be printed directly on the container. By way of example, such instructions accompanying the fragrance card 102 and container 108 may describe the method of use of the instant invention, and indicate the position and size of the windows through use of figures similar to FIG. 9 and FIG. 10, that illustrate the window designator 110a, and/or the additional window designators 116a. Alternatively, or in addition to, the instructions and/or the window designator 110a and additional window designator 116a may be printed directly on the container 108.

Fragrance Card

In a preferred embodiment the fragrance card is an absorbent device to store and disperse the fragrance, by way of example, a simple blotter board. The blotter board may be of any shape or size thereby allowing the individual to choose by aesthetic appeal. In one preferred embodiment the fragrance card that is a blotter board of rectangular shape of approximately 2.125 by 3.375 inches and between 0.062 to 0.25 inches in thickness. In general usage the longitudinal sides are up right orientation by the user. Other shapes envisioned are polygons, triangles, and circles, as well as the shapes of plants, flowers, animals, or known characters including movie or cartoon characters. The fragrance card 2 or blotter board typically has a means for support, preferably a hole 6, through the fragrance card 2 to secure a cord 4 or string for hanging. The cord 4 or string may be comprised of any suitable material known in the art including elastic material. It is anticipated the fragrance card may be decorated with aesthetic designs, perhaps floral patterns to reflect the type of fragrance contained. Alternatively, the fragrance card may contain advertisements of goods or services thought to be useful to the user.

The fragrance card or blotter board may be manufactured from almost any absorbent material. Preferred examples included blotter paper, absorbent paper, and wicking paper, cardboard, perforated and micro perforated paper. Other examples include but are not limited to clay coated paper, cardstock, cardboard, chipboard, fiberboard, polymers, high density polyethylene, polypropylene, polyvinyl chloride, nylon, ferrous and non-ferrous metal foils, their alloys, and composites.

The blotter board or absorbent device may be permeated with fragrances of unlimited variety. Preferred examples are well known in the art and include floral plants and spices. Non-limiting examples of floral fragrances include, azaleas, chamomile, *chrysanthemum, clematis, corylopsis spicata*, crab *pyrus coronaria*, flowering currant, garland flower, honeysuckle, iris, *itea virginica*, jasmine, lavender, lilacs, lilies, *magnolia*, olive, peony, *phlox*, primrose, *pyrus angustifolia, rhododendron, ribes aureum*, rose, *rubus* deliciosus, sweet pea, wallflower, and *yucca*. Non-limiting examples of spices induce allspice, ajwain, anise, black cumin, black pepper, caraway seed, cardamom, *cassia*, cayenne, celery seeds, chili pepper, cinnamon, clove, coriander, cumin, dill, fennel, fenugreek, frankincense, galangal, garlic, ginger, horseradish, jalapeno pepper, juniper berries, licorice, mace, mustard, nutmeg, onion, paprika, peppercorns, saffron, sesame, star anise, sumac, Tabasco pepper, tamarind, and turmeric. Also included are bergamot, bitter gourd, blue gum, bottle gourd, carrot, carrot seed, cashew fruit, cacao, cedar wood, coconut, custard apple, cinnamon bark, clary sage, *eucalyptus*, frankincense, geranium, ginger, *helichrysum italicum* jasmine, lemon, jackfruit, lemongrass, mango, okra, Melissa, neem, oregano, Otto, patchouli, peppermint, pineapple, rosemary, sandalwood, and vanilla.

As many fragrances are poorly soluble in water, in particular the essential oils, the addition of a solvent or carrier oil may prove beneficial in solubilizing the extracts. Solvent solutions known in the art include alcohols, dipropylene glycol, diethyl phthalate, hexylene glycol, water, and so forth. The exact formulation of the solvents and fragrance may be varied to adjust the rate of release of the fragrance. The fragrance card may then be permeated with the fragrance/solvent or fragrance/oil mixture by spraying, dipping, soaking, or any number of means known in the art.

Non-Porous Container and Window Cover

Illustrated in the figures is a non-porous container which also functions as packaging for holding and protecting fragrance card before use. The non-porous nature of the container prevents vaporization of the fragrance. The container may comprise one or more windows to allow vaporization and dispersal of the fragrance during use. The size or area of the window or windows may be predetermined by the manufacturer based on the knowledge of the vaporization rate of the fragrance and the most desirable rate of fragrance release. The vaporization rate of the fragrance may be known based on the particular fragrance/solvent or fragrance/oil combination.

Shown in the figures is a window cover adhesively and reversibly attached to the container so as to cover and seal the one or more windows. The size of the window cover will necessarily be slightly larger than the windows so as to overlap slightly on the container. Preferably, the adhesive is applied only to the window cover. Preferably the adhesive is a tacky adhesive that remains with the container window cover after the window cover is removed. After removal, the window cover may be discarded or reapplied to the container to retain the remaining fragrance if the user desirers.

Methods of making non-porous containers or packaging that enclose fragrance cards are known in the art. A non-limiting example is described in U.S. Pat. No. 7,926,735 incorporated herein by reference in its entirety. The inner dimensions of the non-porous containers will necessarily be slightly larger than the fragrance card to so as to enclose the fragrance card and allow for a small volume of air. The fragrance card may be placed in the container, or the container may be manufactured around the fragrance card. The window may be made in the non-porous material before or after sealing the container, and is made by way of example by cutting. Typically a non-porous container may be constructed from a simple sheet of non-porous material. In the figures are shown one example of a sheet of non-porous material wrapped around the fragrance card with seams that are heat sealed at both ends and on one side of the container. The seams may be sealed preferably by heat sealing, or any appropriate means known in the art including adhesives. Several suitable film materials are known in the art for constructing the non-porous container and/or the windows. Among these are polyethylene terephthalate polyester (commonly referred to as Mylar™), polypropylene film, and cellophane. Those skilled in the art will appreciate the advantages of each with respect to cost, durability, workability, and so forth. The container may be transparent, semi-transparent or opaque. It is anticipated the container may be decorated with aesthetic designs, perhaps floral patterns to reflect the type of fragrance contained. Alternatively, the container may convey advertisements of goods or services thought to be useful to the user.

From the aforementioned description, is a fragrance card and container combination that is uniquely capable of limiting the amount of fragrance dispersed while enabling the user to manipulate the fragrance card with little or no contact with the fragrant oils. As such, those skilled in the art will appreciate that the concept, upon which this disclosure is based, may readily be utilized as a basis for the designing of other structures, methods, and systems for carrying out the several purposes of the present invention. Therefore, the claims include such equivalent constructions insofar as they do not depart from the spirit and the scope of the present invention.

I claim:

1. A fragrance card provided within a multi windowed container and for use for vaporization of a fragrance from said fragrance card at a controlled rate of fragrance released through the selective opening of the multi-windowed container during its usage and application, comprising:
   a fragrance carrying card having a cord appended thereto, said fragrance carrying card being formed of an absorbent material selected from one of blotter paper, absorbent paper, wicking paper, cardboard, and perforated paper, said fragrance carrying card having a shape of one of rectangular, polygon, triangle, circles, in addition to the shape of a plant, flower, animal, or known characters, including movie or cartoon characters;
   said fragrance carrying card being permeated with a fragrance, said fragrance being one of a perfume, the aroma of a floral plant, and a spice;
   said fragrance being mixed with one of a solvent and carrier oil to solubilize said fragrance to attain its absorbance within said fragrance card, said solvent being one of alcohol, propylene glycol, diethyl phthalate, hexylene glycol, and water, and a carrier oil which solubilizes the fragrance to attain its absorbance within said fragrance card;

a non-porous container, said non-porous container being formed of one of polyethylene terephthalate polyester, polypropylene film, and cellophane, with said container having a top, bottom, and a front and back therefor, and having more than one formed window provided within the container front and back thereof, said container being larger than said fragrance card to contain said fragrance card therein, said container window being smaller than said fragrance card, and said fragrance card contained within said non-porous container;

said non-porous container having said front and back wall formed windows to limit and control the vaporization of the fragrance from said fragrance card, at least one of said formed windows being formed at the top of said container, the top of said container having a first window designator to indicate where the container is to be cut at downwardly from its top thereof, the window designator having a predetermined shape, the top of the container capable of being cut within its upper side edges to limit the extent of upward movement of the fragrance carrying card relative to the non-porous container in which it locates, and after cutting, said cord being pulled for shifting the fragrance card upwardly within the container to provide for its partial exposure to attain controllable vaporization and to disseminate its fragrance to the ambient air;

whereby the user cuts the top of the container to open said formed window to attain access to the cord through said formed window and using the cord to pull the fragrance card upwardly and to suspend it with the non-porous container to allow controlled release of the fragrance from the fragrance card into the surrounding atmosphere;

said non-porous container having said front, and another of said formed window being arranged upon the front of the non-porous container, and a non-porous window cover adhesively and reversibly attached to the container so as to cover the formed window and the cord, and to provide a non-porous seal that is contiguous with the container;

said window cover may be at least partially removed, said cord of the fragrance card pulled through the formed window, for suspension of the fragrance card and said non-porous container that holds said fragrance card for select controlled rate of release of the fragrance from the fragrance card into the surrounding atmosphere;

the bottom of said non-porous container having a second window designator of another provided proximate the bottom thereof, to indicate where the user cuts the bottom of the container to provide a predetermined additional window for providing a further predetermined controlled vaporization and a further full release of the fragrance from the fragrance carrying card into the surrounding atmosphere;

a first heat seal formed in the top of the container and a second heat seal formed in the bottom of the container, the first window designator extends past the first heat seal, and the second window designator is adjacent to the second heat seal;

said heat seal formed in the top of the container and the shape of the first window designator extends past the heat seal, and wherein the second window designator is adapted to be cut at the bottom of the container and removed from the container in the second shape, and once removed from the container, the fragrance card is exposed to attain controllable and increased vaporization of the fragrance and to disseminate the fragrance to ambient air.

* * * * *